United States Patent
Tomoeda

(10) Patent No.: US 11,000,258 B2
(45) Date of Patent: May 11, 2021

(54) NONINVESIVE ARTERIOVENOUS PRESSURE MEASUREMENT DEVICE AND ARTERIOVENOUS PRESSURE MEASUREMENT METHOD USING THE MEASUREMENT DEVICE

(71) Applicant: Kurume University, Fukuoka (JP)

(72) Inventor: Hiroshi Tomoeda, Fukuoka (JP)

(73) Assignee: Kurume University, Fukuoka (JP)

( * ) Notice: Subject to any disclaimer, the term of this patent is extended or adjusted under 35 U.S.C. 154(b) by 581 days.

(21) Appl. No.: 15/757,617

(22) PCT Filed: Sep. 7, 2016

(86) PCT No.: PCT/JP2016/076323
§ 371 (c)(1),
(2) Date: Mar. 5, 2018

(87) PCT Pub. No.: WO2017/043536
PCT Pub. Date: Mar. 16, 2017

(65) Prior Publication Data
US 2018/0242945 A1    Aug. 30, 2018

(30) Foreign Application Priority Data

Sep. 8, 2015 (JP) ................................. 2015-176249
Dec. 16, 2015 (JP) ............................. JP2015-245177

(51) Int. Cl.
*A61B 8/04* (2006.01)
*A61B 5/022* (2006.01)
(Continued)

(52) U.S. Cl.
CPC ................ *A61B 8/04* (2013.01); *A61B 5/022* (2013.01); *A61B 5/023* (2013.01); *A61B 8/4455* (2013.01);
(Continued)

(58) Field of Classification Search
CPC ........... A61B 8/04; A61B 5/022; A61B 5/023; A61B 8/4455; A61B 5/02152;
(Continued)

(56) References Cited

U.S. PATENT DOCUMENTS 6,086,533 A * 7/2000 Madsen ............... A61B 5/0053
600/438
6,309,354 B1 10/2001 Madsen et al.
(Continued)

FOREIGN PATENT DOCUMENTS

CN    102743246 A    10/2012
CN    204411453 U    6/2015
(Continued)

OTHER PUBLICATIONS

International Preliminary Report on Patentability for PCT/JP2016/076323 dated Mar. 13, 2018.
(Continued)

*Primary Examiner* — Sanjay Cattungal
(74) *Attorney, Agent, or Firm* — Knobbe Martens Olson & Bear LLP

(57) ABSTRACT

The present invention provides an arteriovenous pressure measurement device which allows noninvasive and accurate measurement of arteriovenous pressure, and also provides an arteriovenous pressure measurement method using the measurement device. The noninvasive arteriovenous pressure measurement device comprises a probe (20) for radiating ultrasound toward a blood vessel in the skin, a pressing part (10) for pressing the skin in a state of being placed between the skin and the probe (20), and a pressure sensor (33) for detecting a pressing force applied to the skin at the pressing part (10), the pressing part (10) having water (36) permeable to the ultrasound and a balloon (31) accommodating the water (36), the flexible container (31) being made
(Continued)

of a flexible material permeable to the ultrasound, and an outer surface of the balloon (31) presses the skin.

7 Claims, 3 Drawing Sheets

(51) Int. Cl.
    *A61B 5/023*         (2006.01)
    *A61B 8/00*          (2006.01)
    *G01L 11/06*        (2006.01)
    *G01L 17/00*        (2006.01)
    *G01S 15/89*         (2006.01)

(52) U.S. Cl.
    CPC .............. *G01L 11/06* (2013.01); *G01L 17/00* (2013.01); *G01S 15/8906* (2013.01)

(58) Field of Classification Search
    CPC ........ A61B 2560/0406; A61B 5/02141; A61B 5/02208; A61B 5/447; A61B 5/1495; A61B 2562/0247; G01L 11/06; G01L 17/00; G01S 15/8906
    See application file for complete search history.

(56) References Cited

U.S. PATENT DOCUMENTS

| | | | | |
|---|---|---|---|---|
| 9,528,893 | B2 * | 12/2016 | Wang | ........................ G02B 6/30 |
| 2002/0052550 | A1 | 5/2002 | Madsen et al. | |
| 2007/0270720 | A1 * | 11/2007 | Fry | .......................... A61B 8/04 600/587 |
| 2012/0165686 | A1 * | 6/2012 | Masuda | ................. A61B 8/485 600/485 |
| 2013/0223193 | A1 * | 8/2013 | Takahashi | ............. B06B 1/0622 367/140 |
| 2013/0225993 | A1 * | 8/2013 | Takahashi | ................ A61B 8/54 600/438 |
| 2015/0112214 | A1 * | 4/2015 | Mizukami | ............ A61B 8/0891 600/490 |
| 2015/0238169 | A1 * | 8/2015 | Mizukami | ............ A61B 8/5223 600/449 |
| 2015/0243190 | A1 * | 8/2015 | Murai | ...................... A61B 8/04 600/438 |

FOREIGN PATENT DOCUMENTS

| | | |
|---|---|---|
| EP | 2196141 A1 | 6/2010 |
| JP | 2005-28123 A | 2/2005 |
| JP | 2005-34543 A | 2/2005 |
| JP | 2013-188382 A | 9/2013 |
| WO | WO 85/00278 A1 | 1/1985 |
| WO | WO 99/63890 A1 | 12/1999 |
| WO | WO 2015/103472 A1 | 7/2015 |

OTHER PUBLICATIONS

Thalhammer, Christoph et al., "Noninvasive Central Venous Pressure Measurement by Controlled Compression Sonography at the Forearm" Journal of the American College of Cardiology, 2007, pp. 1584-1589, vol. 50, No. 16.

International Search Report for PCT/JP2016/076323 dated Oct. 25, 2016.

Supplementary European Search Report for EP 16844397 dated Mar. 12, 2019.

\* cited by examiner

NONINVESIVE ARTERIOVENOUS PRESSURE MEASUREMENT DEVICE AND ARTERIOVENOUS PRESSURE MEASUREMENT METHOD USING THE MEASUREMENT DEVICE

CROSS REFERENCE TO RELATED APPLICATIONS

This application is a U.S. National Phase Application of PCT International Application Number PCT/JP2016/076323, filed on Sep. 7, 2016, designating the United States of America and published in the Japanese language, which is an International Application of and claims the benefit of priority to Japanese Patent Application No. 2015-176249, filed on Sep. 8, 2015, and Japanese Patent Application No. 2015-245177, filed on Dec. 16, 2015. The disclosures of the above-referenced applications are hereby expressly incorporated by reference in their entireties.

TECHNICAL FIELD

The present invention relates to an arteriovenous pressure measurement device which allows noninvasive and accurate measurement of arteriovenous pressure.

BACKGROUND ART

Measurement of arteriovenous pressure (arterial pressure and venous pressure) serves as an indicator for determining therapeutic strategy based on judgement of deficiency or excess of the amount of circulating blood or judgement of right cardiac failure in the fields of emergency and intensive medical care, for example. In addition, the use of such a measurement in the fields of vascular surgery, dermatology, etc. is anticipated, and an example of such use is venous pressure measurement in a leg of a patient having a varix in the leg.

Conventional arteriovenous pressure measurement methods, as invasive measurement methods, need, for example, a procedure as follows: a needle puncture is made into or a catheter is inserted and guided to a blood vessel at a measurement site, a drip route to the inserted needle or catheter is filled with a liquid, and a pressure sensor is attached thereto. Therefore, the measurement takes considerable time and may cause delayed treatment in the field of time-critical emergency medical care. In addition, as described above, the conventional methods involving blood vessel puncture or catheter insertion are highly invasive for patients (see Patent Literature 1).

In addition, these invasive treatments involve risks of cardiovascular damage, bleeding, bloodstream infection, pneumothorax, and hemothorax. In addition, the patient as a subject of the measurement is basically hooked up to a drip route and may have difficulties in moving around. As a measure to overcome such disadvantages, Non Patent Literature 1 discloses a venous pressure measurement device for noninvasively measuring venous pulse pressure using an ultrasound measurement probe and using vein collapse resulting from pressing the skin, without needle puncture to the blood vessel.

In this venous pressure measurement device, a disk-like silicone object is attached onto the surface of the ultrasound probe. The silicone object is placed on the skin just above the vein to be measured, and the ultrasound probe is pressed against the skin to induce vein collapse. The silicone object is permeable to ultrasound and does not interrupt the ultrasound from the ultrasound probe. Therefore, an image of the collapsed vein can be obtained using the ultrasound probe.

Between the ultrasound probe and the silicone object, a pressure sensor is disposed to measure the pressing force applied via the ultrasound probe to the skin. By the pressure sensor, the pressing force that has resulted in vein collapse is detected as a venous pressure.

CITATION LIST

Patent Literature

Patent Literature 1: JP 2013-188382 A

Non Patent Literature

Non Patent Literature 1:
Christoph Thalhammer et al., "Noninvasive Central Venous Pressure Measurement by Controlled Compression Sonography at the Forearm", Journal of the American College of Cardiology, Elsevier Inc.

SUMMARY OF INVENTION

Technical Problem

However, in the case of the noninvasive venous pressure measurement device disclosed in Non Patent Literature 1, when the vein of which the venous pressure is desired to be measured is present, for example, in a greatly curved portion, such as the forearm or the front of the lower leg, accurate measurement cannot be achieved because the disk-like silicone object is not entirely in contact with the body surface, i.e., the central part of the silicone object as the pressure measurement part is compressed by the greatly curved portion and deformed whereas the rest of the silicone object is not in contact with the body.

Also, the disk-like silicone object as the pressure measurement part of the measurement device is thin, and therefore, when the device is pressed against the part to be measured, the silicone object on the surface of the device can be brought into direct contact with the ultrasound probe or the pressure sensor, causing variation in the measured values. In particular, when the part to be measured is greatly curved as described above, this problem can be significant, resulting in inaccurate measurement.

The present invention was made in light of the problems of the noninvasive venous pressure measurement device disclosed in Non Patent Literature 1, and an objective of the present invention is to provide an improved arteriovenous pressure measurement device which allows noninvasive and accurate measurement of arteriovenous pressure, i.e., not only venous pressure but also arterial pressure, which is basically unmeasurable with the venous pressure measurement device of Non Patent Literature 1. Another objective of the present invention is to provide an arterial pressure measurement method using the measurement device.

Solution to Problem

The present invention is premised on a noninvasive arteriovenous pressure measurement device. The noninvasive arteriovenous pressure measurement device comprises a probe (20) for radiating ultrasound toward a blood vessel in the skin, a pressing part (10) for pressing the skin in a state of being placed between the skin and the probe (20), and a detecting part (33) for detecting a pressing force applied to the skin at the pressing part (10), the pressing part (10) having a liquid (36) permeable to the ultrasound and a flexible container (31) accommodating the liquid (36), the flexible container (31) being made of a flexible material permeable to the ultrasound, and a part of the outer surface of the flexible container (31), the part being in the path of the ultrasound, presses the skin.

In a preferred noninvasive arteriovenous pressure measurement device of the present invention, the detecting part (33) detects the pressure of the liquid (36) in the flexible container (31) as the pressing force.

In a preferred noninvasive arteriovenous pressure measurement device of the present invention, the pressing part (10) comprises an advancing and retreating mechanism (85) for advancing and/or retreating the probe (20) relative to the flexible container (31).

In a preferred noninvasive arteriovenous pressure measurement device of the present invention, the pressing part (10) comprises a pressing button (32) for pressing the outer surface of the flexible container (31) at a part not in contact with the skin.

In a preferred noninvasive arteriovenous pressure measurement device of the present invention, the pressing part (10) comprises a stretchable bag-like object (70) in the flexible container (31) accommodating the liquid (36) and a fluid passage (71) for allowing a fluid (72) to flow into or out of the bag-like object (70).

In a preferred noninvasive arteriovenous pressure measurement device of the present invention, the fluid passage (71) comprises a back-pressure regulating part (73) for regulating the back pressure of the fluid, and the inner pressure of the bag-like object (70) is regulated by the back-pressure regulating part (73).

In a preferred noninvasive arteriovenous pressure measurement device of the present invention, the fluid passage (71) has an outlet port for allowing the fluid to flow out of the bag-like object (70).

In a preferred noninvasive arteriovenous pressure measurement device of the present invention, a casing (11) accommodating the flexible container (31) is provided, the casing (11) has a contact surface (25) to be brought into contact with the skin, an ultrasound passing aperture (15) is formed on the contact surface (25) to allow the ultrasound that has passed through the flexible container (31) and the liquid (36) to pass the aperture, the outer surface of the flexible container (31) presses the skin through the ultrasound passing aperture (15), and the outer periphery of the ultrasound passing aperture (15) has an elliptical shape, a rectangular shape, or a rectangle-like shape having four rounded corners.

In a preferred noninvasive arteriovenous pressure measurement device of the present invention, the flexible container (31) has a tubular shape, and a flanged portion (42) is formed at one axial end of the flexible container (31) to allow close contact with the outer periphery of the ultrasound passing aperture (15) on the inner surface of the casing (11).

In an arteriovenous pressure measurement method using the noninvasive arteriovenous pressure measurement device of the invention, the device comprising a probe (20) for radiating ultrasound toward a blood vessel in the skin, a pressing part (10) for pressing the skin in a state of being placed between the skin and the probe (20), a detecting part (33) for detecting a pressing force applied to the skin at the pressing part (10), and an image processor, the pressing part (10) having a liquid (36) permeable to the ultrasound and a flexible container (31) accommodating the liquid (36), the flexible container (31) being made of a flexible material permeable to the ultrasound, the method comprises pressing the skin with a part of the outer surface of the flexible container (31), the part being in the path of the ultrasound, radiating ultrasound toward a blood vessel in the skin to obtain echo signals from reflected ultrasound, scanning and processing the echo signals using the image processor to obtain a B-mode image, arithmetically processing a plurality of frames of the B-mode image using the image processor to extract the intensities of certain frequency components for obtaining a pulsating frequency, and determining a diastolic pressure and a systolic pressure of the artery based on the pressure value detected by the detecting part (33) and the pulsating frequency. In the present invention, the diastolic blood pressure means the lowest blood pressure, and the systolic blood pressure means the highest blood pressure. The image processor may be one capable of the scanning and the arithmetic processing, and a commercially marketed computer suitable for the present invention may be adopted.

Advantageous Effects of Invention

According to the present invention, since the skin is pressed with a part of the outer surface of the flexible container containing a liquid, the part being in the path of the ultrasound, greater transformation of the outer surface of the flexible container can be achieved as compared to the outer surface of a flexible member not containing a liquid, so called a solid flexible member. The greater transformation of the outer surface of the flexible container allows the outer surface to well fit to the skin of a greatly curved portion, such as the forearm or the front of the lower leg, when the outer surface of the flexible container is pressed against the skin.

Therefore, the skin can be pressed in a condition where the outer surface of the flexible container well fits to the skin of a greatly curved portion, and as a result, the arteriovenous pressure in the curved portion can be accurately measured.

Thus, according to the present invention, noninvasive and accurate measurement of not only venous pressure but also arterial pressure using an ultrasound probe can be achieved. A conventional blood pressure monitor needs a considerable measurement time because of the procedure in which a cuff is put around the upper arm, the pressure of the cuff is increased, and then measurement is performed while the pressure of the cuff is gradually decreased. In contrast, with the measurement device of the present invention, which is of a pressure-increasing type, an approximate arterial pressure and venous pressure can be immediately predicted by observing changes in the images of the artery and vein while increasing the applied pressure. Therefore, the measurement device of the present invention can reduce the pressurization time. That is, in contrast to conventional blood pressure monitors, the measurement device of the present invention does not need time for pressurization exceeding the intended measurement value, and as a result, the measurement time can be reduced to ½ to ⅙ of that of a conventional blood pressure monitor.

BRIEF DESCRIPTION OF DRAWINGS

FIG. 5 shows outer shapes of the balloon of Modification Example 2.

DESCRIPTION OF EMBODIMENTS

Figure 1:
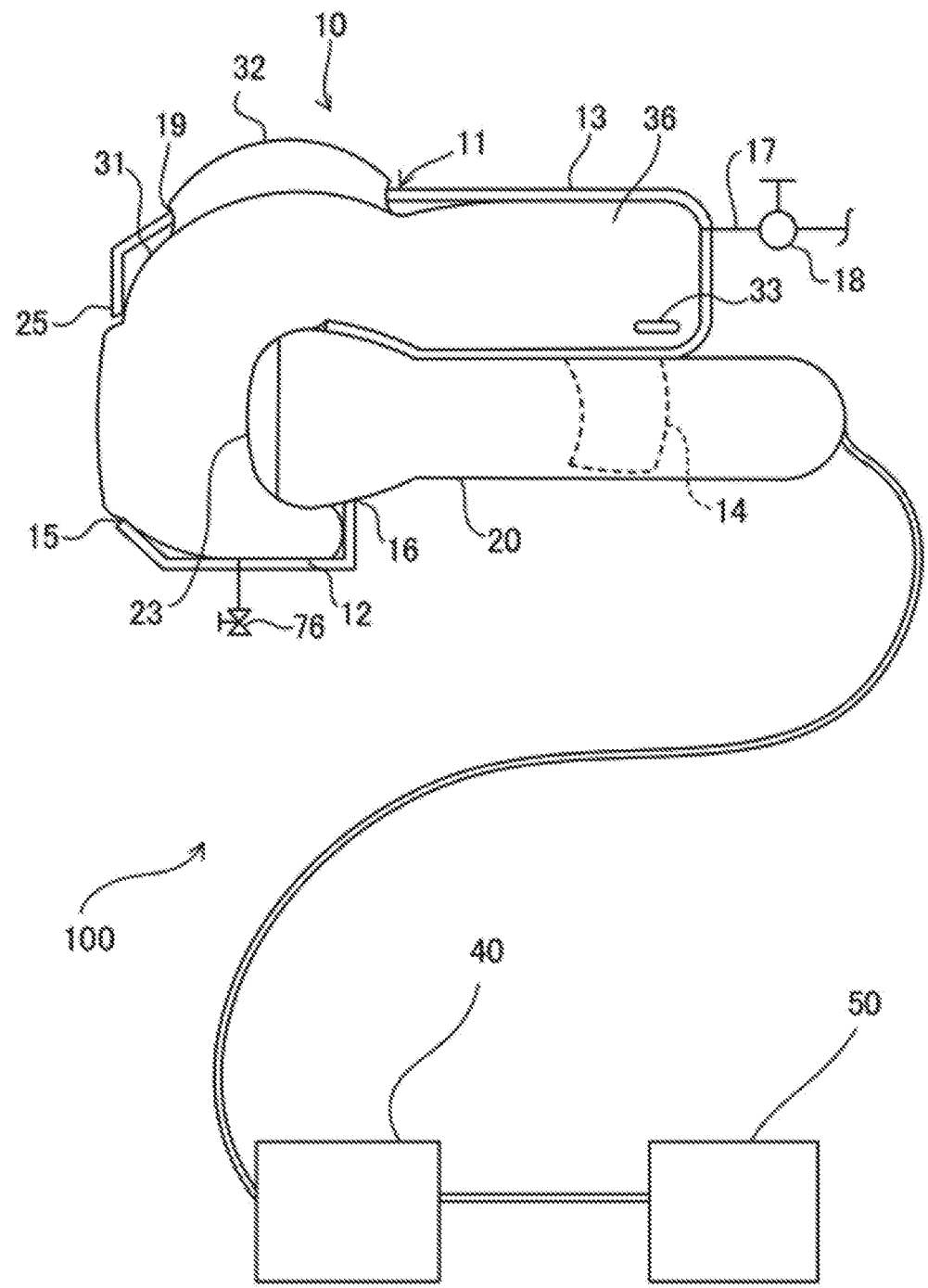
FIG. 1 shows a first embodiment of the noninvasive arteriovenous pressure measurement device of the present invention.

Hereinafter, embodiments of noninvasive arteriovenous pressure measurement device (100) of the present invention will be described in detail based on the drawings. The embodiments described below are merely illustrative examples, and the noninvasive arteriovenous pressure measurement device of the present invention is not limited thereto.

The first embodiment of the noninvasive arteriovenous pressure measurement device (100), in contrast to conventional measurement devices which is usually used in a procedure involving needle puncture to an artery or a vein for measuring the pressure, allows pressure measurement without needle puncture to the blood vessel and can be used for both arterial pressure measurement and venous pressure measurement without needing any other device. Hereafter, the fields where the device can be used will be described.

First, measurement of venous pressure will be described although measurement of venous pressure only is already described in Non Patent Literature 1. The significance of the venous pressure measurement is already partly written in Non Patent Literature 1, but will be described again.

In the first place, such a venous pressure measurement can be used in the fields of emergency and intensive medical care. Central venous pressure, which is measured in these fields, is an important indicator for determining therapeutic strategy based on judgement of deficiency or excess of the amount of circulating blood or judgement of right cardiac failure. Generally, a catheter for measuring central venous pressure is inserted by an invasive procedure from cervical, subclavian, or inguinal region etc. into the superior caval vein or inferior caval vein, and the pressure is measured with a pressure sensor. In the insertion of the catheter, a procedure involving disinfection, puncture, positioning of the catheter, positioning of the sensor, etc. is necessary, and it takes at least several minutes before the measurement. Also, in some cases, the insertion of the catheter itself is difficult.

With use of the first embodiment of the noninvasive arteriovenous pressure measurement device (100), a value approximately equal to central venous pressure can be determined in an extremely simple and convenient manner and in a short period of time by only pressing the external jugular vein of a patient in the supine position. Except in the special cases of, such as, occlusion or coarctation due to a blood clot or compression between the external jugular vein and the superior caval vein, the intended measurement of the venous pressure can be noninvasively achieved in a few seconds. Therefore, in time-sensitive situations where urgent treatment is required, time to the start of the treatment is extremely shortened.

Next, in echocardiography for detailed cardiac examination, especially in the measurement of right-sided pressure, the measurement of central venous pressure is useful. When systolic right ventricular pressure or pulmonary artery pressure is determined by echocardiography, the reverse flow velocity V (m/s) of the blood flowing back from the right ventricle through the tricuspid valve into the right atrium during systole is measured, and the systolic pressure gradient [P] between the right ventricle and the right atrium is calculated by the formula of $P=4V^2$.

The sum of the right ventricle-right atrium pressure gradient and the right atrial pressure is generally adopted as a presumed right ventricular pressure or pulmonary artery pressure. In a current examination, the right atrial pressure is generally presumed to be 5 mmHg or 10 mmHg, and the value obtained by simply adding 5 mmHg or 10 mmHg to the right ventricle-right atrium pressure gradient is generally adopted as a presumed right ventricular pressure. In some cases, the right atrial pressure presumed based on the diameter of the inferior caval vein is added to the right ventricle-right atrium pressure gradient to give a presumed right ventricular pressure. The method in which 5 mmHg or 10 mmHg is simply added to the right ventricle-right atrium pressure gradient is usually not disadvantageous in most cases where the patient does not have dehydration, overhydration, cardiac failure, or the like, because such a patient actually has the right ventricular pressure almost the same as the value presumed in the way. However, in a patient in need of urgent treatment or having cardiac failure, the right atrial pressure can be different from a normal value (5 mmHg or 10 mmHg), and therefore, the measurement of central venous pressure is desirable.

In the presumption of the right atrial pressure based on the diameter of the inferior caval vein, due to various factors including the body shape and right cardiac failure, the presumed value can be greatly different from the actual right atrial pressure. By using the value of central venous pressure measured with the newly developed noninvasive arteriovenous pressure measurement device instead of the unreliable right atrial pressure value that has been used so far, the right ventricular pressure, which has been calculated as a rough reference value, can be almost exactly calculated from echography only.

Other possible usages include the measurement of venous pressure in a leg or in other superficial veins in the fields of vascular surgery, dermatology, etc. An example of such use is venous pressure measurement in a leg of a patient having a varix in the leg.

Fatigue, pain, cramp, skin ulcer, skin pigmentation, etc. in a leg associated with a varix in the leg are considered to be caused by continuously rising venous pressure in the leg during standing, and the cause is considered to be functional incompetence of a valve for backflow prevention in the leg vein. Both in a healthy person without any disease in the leg veins and in a patient having a varix in the leg, the venous pressure during standing is elevated due to the influence of gravity.

However, in cases where a healthy person performs a leg exercise, the massage effect on the vein by muscles pushes the blood in the vein with valves for backflow prevention in the cranial direction against gravity, and the venous pressure in the leg falls immediately after the exercise.

In contrast, in the cases of a patient having a varix, due to the functional incompetence of a valve for backflow prevention, the blood cannot be easily pushed up in the direction of the heart, and the venous pressure does not sufficiently fall. Currently, to measure the venous pressure, puncture to the leg vein immediately after the exercise or exercise performed with venipuncture is required, which is practically difficult.

With use of the first embodiment of the noninvasive arteriovenous pressure measurement device (100), local venous pressure measurement can be achieved in a few seconds. Also, in contrast to the venous pressure measurement device shown in a photograph in Non Patent Literature 1, with which errors occur in the measurement of arteriovenous pressure at 50 mmHg or higher, the first embodiment of the noninvasive arteriovenous pressure measurement device (100) is capable of measuring a further higher venous pressure.

The reason why the first embodiment of the noninvasive arteriovenous pressure measurement device (100) is capable of measuring a higher venous pressure than the venous pressure measurement device in Non Patent Literature 1 is as follows. In the case of the venous pressure measurement device in Non Patent Literature 1, as describe above, it is sometimes difficult to fit the silicone object to the site to be measured. In contrast, in the case of the first embodiment of the noninvasive arteriovenous pressure measurement device (100), as described later, it is possible to well fit the balloon (31) to the site to be measured, and as a result, the pressing force applied by the balloon (31) can be transmitted with certainty to the site to be measured.

Therefore, the noninvasive arteriovenous pressure measurement device (100) of the first embodiment is useful in determining whether the clinical symptoms in the leg of a patient having a varix in the leg whose venous pressure is prone to rise are attributable to the rise in the venous pressure. In addition, it is possible to use the measured pressure as an indicator for the prediction before surgery whether the surgery of a varix in the leg is effective for the improvement in the clinical symptoms.

Next, with use of the noninvasive arteriovenous pressure measurement device (100), arterial pressure measurement, which is considered to be difficult with use of the device of Non Patent Literature 1, can be noninvasively achieved. The reason is, as described later, that it is possible to well fit the outer surface of the balloon (31) to the surface of the site to be measured, and as a result, the pressing force applied by the balloon (31) can be transmitted with certainty to the site to be measured, and that the pressing force by the balloon (31) can raise the inner pressure of the balloon to approximately 200 mmHg, which greatly exceeds 70 mmHg as the upper limit of measurable pressure for the venous pressure measurement device of Non Patent Literature 1. Basically, measurable arteries are major arteries at sites where the pulsation is palpable from on the surface of the skin, and intended arteries include the radial artery, the brachial artery, the carotid artery, etc. By measuring a local arterial pressure, decrease in the perfusion pressure associated with coarctation or occlusion in the artery can be measured in a simple and convenient manner.

Also, the measurement of an arterial pressure of a nutrient artery or the like just under the skin is also possible, and data collected with the device are potentially useful for judging whether the skin is prone to pressure ulcers. Other examples of the use of this device associated with arterial pressure measurement include predicting whether the skin at the site of leg amputation as a result of avascular necrosis will become susceptible to protracted wound healing due to ischemia of the skin.

Currently, in the prediction of whether the skin at the site of leg amputation as a result of avascular necrosis in the leg will become susceptible to protracted wound healing, an expensive medical device capable of measuring skin perfusion pressure, which is priced at millions of yen, is used for the judgement. However, with the first embodiment of the noninvasive arteriovenous pressure measurement device (100), the arterial pressure of a nutrient artery of the skin and the venous pressure of veins in the vicinity can be noninvasively measured, and the arterial pressure and the venous pressure can be correlated with the skin perfusion pressure.

In a facility already having an echo machine, by only mounting the pressing part (10) of the noninvasive arteriovenous pressure measurement device (100) to the echo probe, it becomes possible to predict protracted wound healing of the skin at the site of leg amputation as a result of avascular necrosis in the leg.

The first embodiment of the noninvasive arteriovenous pressure measurement device (100) comprises, as shown in FIG. 1, a probe (20) for radiating ultrasound toward a blood vessel in the skin, a pressing part (10) for pressing the skin in a state of being placed between the skin and the probe (20), and a pressure sensor (33) as a detecting part for detecting a pressing force applied to the skin at the pressing part (10).

The pressing part (10) comprises a liquid (36), a balloon (31) as a flexible container accommodating the liquid (36), and a casing (11) accommodating the balloon (31), and a pressing button (32) for pressing the balloon (31).

The liquid (36) is permeable to the ultrasound from the probe (20), and in the first embodiment, the liquid (36) is water. However, the liquid (36) is not limited to water, and may be any liquid as long as it is permeable to the ultrasound from the probe (20).

The balloon (31) is formed of silicone or a silicone resin, which is a flexible material. However, the material for forming the balloon (31) is not necessarily silicone or a silicone resin, and may be any material as long as it is permeable to ultrasound. The material may be, for example, latex (rubber) or the like.

The casing (11) has a cover part (12) and an extended part (13). The cover part (12) is located at the side facing the head part (23) of the probe (20). The extended part (13) extends from the cover part (12) along the handle of the probe (20). The extended part (13) of the casing (11) is provided with a clamping piece (14) to support the handle of the probe (20) by clamping. Thus, the casing (11) of the pressing part (10) and the probe (20) are securely fastened to each other. However, the casing (11) is not limited to one that can be detachably fixed to the probe (20), and may be integrally formed with the probe (20).

Also, the cover part (12) of the casing (11) has openings, i.e., a probe insertion opening (16), an echo window (15) as an ultrasound passing aperture, and a pressing button mounting opening (19).

Into the probe insertion opening (16), the head part (23) of the probe (20) is inserted. The ultrasound is send from and received at the head part (23). The cover part (12) of the casing (11) has a contact surface (25) to be brought into contact with the skin, and the echo window (15) opens on the contact surface (25). The echo window (15) is located opposite to the above-mentioned probe insertion opening (16). The ultrasound radiated from the head part (23) of the probe (20) penetrates the balloon (31) and the liquid (36), and passes through the echo window (15) to reach the skin.

The outer periphery of the echo window (15) has an elliptical shape. For measuring the arteriovenous pressure in an arm or leg, the echo window (15) is brought into contact with the skin of the arm or leg in such a manner that the major axis of the echo window (15) coincides with the longitudinal direction of the arm or leg. This allows the echo window (15) to entirely contact the skin unlike the case where the echo window (15) has a circular shape. The echo window (15) is not limited to an elliptical shape, and may be, for example, has a rectangular shape or a rectangle-like shape having four rounded corners.

The pressing button (32) is provided in the pressing button mounting opening (19) on the upper side of the cover part (12) of the casing (11). The bottom of the pressing button (32) is in contact with the upper surface of the balloon (31). The pressing button (32) presses the outer surface of the balloon (31), at a part not to be in contact with the skin. When the pressing button (32) is pushed inward from the outside of the casing (11), a part of the balloon (31) in contact with the pressing button (32) is dented. At the same time, another part bulges outward from the echo window (15), and the bulged surface presses the skin. The ultrasound passes through the bulged surface.

The pressure sensor (33) is provided in the balloon (31). As described above, since the skin is pressed via the balloon (31), the pressing force of the balloon (31) can be measured by measuring the inner pressure of the balloon (31).

A tube (17) is connected to the balloon (31). The liquid (36) is supplied to and discharged from the balloon (31) through the tube (17). The tube (17) has a liquid volume regulating valve (18) attached thereto. With the liquid volume regulating valve (18), the volume of the liquid (36) supplied to or discharged from the balloon (31) is regulated.

An air vent valve (76) is provided to the balloon (31). When the liquid (36) is injected into the balloon (31), by opening the air vent valve (76), the liquid (36) can be injected into the balloon (31) while the air in the balloon (31) is allowed to go out through the air vent valve (76). In this way, it is possible to inject only the liquid (36) into the balloon (31).

For measuring the arteriovenous pressure with the arteriovenous pressure measurement device (100), first, the echo window (15) of the pressing part (10) is pressed against the skin. Next, the echo window (15) is kept pressed against the skin, and while the pressing button (32) is held down, ultrasound is radiated from the probe (20).

When the pressing button (32) is pressed, the balloon (31) protrudes or bulges outward from the echo window (15), and the bulged balloon (31) presses the skin. At this time, since the skin is pressed with the outer surface of the balloon (31) containing the liquid (36), greater transformation of the outer surface of the balloon (31) can be achieved as compared to the outer surface of a solid flexible member not containing the liquid (36), allowing the skin to be pressed in a state where the outer surface of the balloon (31) and the outer surface of the skin more favorably fit to each other. The pressurization in the balloon (31) necessary for the balloon (31) to bulge outward from the echo window (15) is not necessarily accomplished by pressing the pressing button (32). Alternatively, the pressurization may be accomplished by supplying pressurized water into the balloon (31) through the tube (17) connected to the balloon (31).

The noninvasive arteriovenous pressure measurement device (100) is also provided with, in addition to the probe (20) having the pressing part (10) mounted thereon, a processing part (40) and a display (50) (see FIG. 1). The probe (20) is electrically connected to the display (50) via the processing part (40).

The processing part (40) converts electric signals coming from the probe (20) and the pressure sensor (33) of the pressing part (10), and transmits the converted electric signals to the display (50).

The display (50) shows, based on the converted electric signals, an image of an artery or a vein, and a value detected by the pressure sensor (33).

Figure 2A:
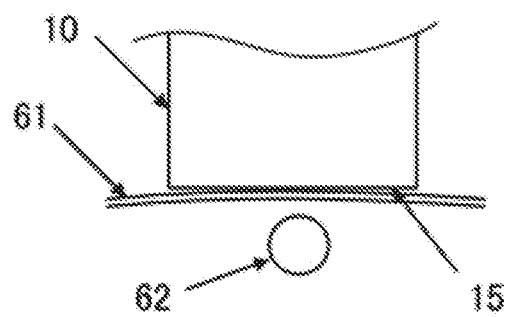
In FIG. 2A, the vein is before collapsing; and in FIG. 2B, the vein is collapsed.

As shown in FIG. 2A, the user brings the echo window (15) of the pressing part (10) into contact with the skin (61). At this time, the blood vessel (62) is not yet pressed. That the blood vessel (62) is not pressed can be confirmed on the display (50).

Figure 2B:
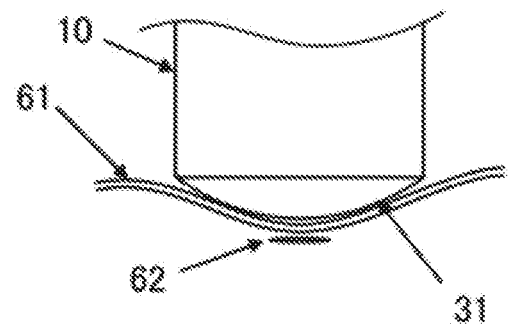
FIG. 2 shows the states of a blood vessel before and after collapsing.

The pressing button (32) of the pressing part (10) is pressed to press the skin (61). At this time, the pressing force applied on the pressing button (32) is regulated so as to gradually press the skin (61). That the blood vessel (62) is collapsing as the skin (61) is gradually pressed by the pressing part (10) can be checked on the display (50). Also, as shown in FIG. 2B, the detection value of the pressure sensor (33) at the moment when the blood vessel (62) collapses, i.e., the pressure value in the balloon (31), can be checked as the venous pressure of the blood vessel (62).

Here, collapse of the blood vessel (62) means the following. When the blood vessel (62) is pressed from the skin surface, the pressed side of the blood vessel (62) comes closer to the opposite side of the blood vessel (62), the blood in the blood vessel (62) moves away, and due to the absence of the blood in the blood vessel (62), the pressed-side wall and the opposite-side wall of the blood vessel (62) are brought into contact with each other, resulting in vein collapse. In the first embodiment, at the time when the pressure in the balloon (31) becomes equal to or slightly higher than the blood pressure in the blood vessel (62), vein collapse occurs.

Since the head part (23) of the probe (20) is hard, when the head part (23) as an ultrasound transmitting and receiving surface of the probe (20) is directly pressed against the skin (61) to induce collapse of a blood vessel (62), thin veins and/or low-pressure veins tend to collapse due to compression by the head part (23), and as a result, collapsed veins may potentially be overlooked, not being regarded as veins.

The balloon (31) of the pressing part (10) is more flexible than the head part (23) of the probe (20), and therefore, the blood vessel (62) immediately below the skin (61) is less likely to easily collapse. For this reason, by controlling the pressing button (32) of the pressing part (10), the blood vessel (62) can be collapsed by a uniform pressing force. Thus, undesired collapse of the blood vessel (62) can be prevented.

Modification Example 1 of the First Embodiment

The Modification Example 1 of the noninvasive arteriovenous pressure measurement device (100a) is different from the first embodiment of the noninvasive arteriovenous pressure measurement device (100) in the points of the addition of a means to pressurize the balloon (31) and of the arrangement of the pressure sensor (33). In the Modification Example 1 of the noninvasive arteriovenous pressure measurement device (100a), the added means to pressurize the balloon (31) enables the measurement of arterial pressure in addition to the measurement of venous pressure. Hereinafter, the differences will be described.

In the cases where the inner pressure of the balloon (31) cannot be increased sufficiently for the measurement of arterial pressure and/or venous pressure in the first embodiment of the noninvasive arteriovenous pressure measurement device (100), the Modification Example 1 of the noninvasive arteriovenous pressure measurement device (100a) is effective.

Figure 3:
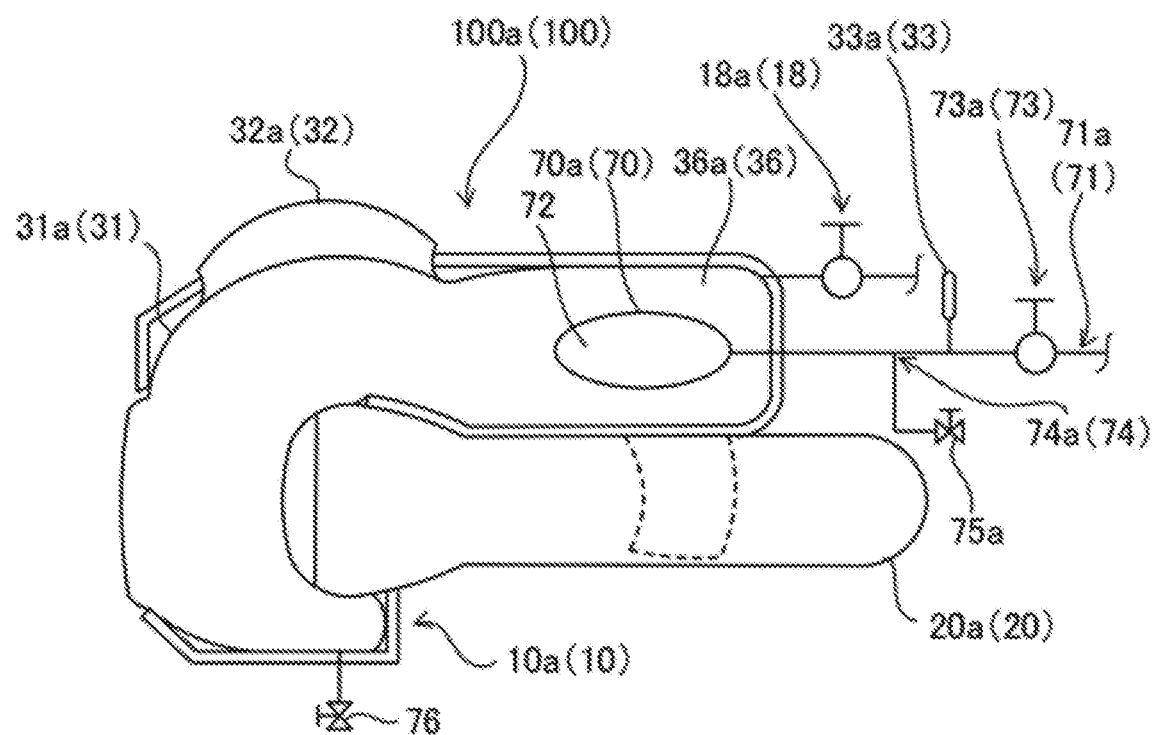
FIG. 3 shows the main part of Modification Example 1 of the first embodiment of the noninvasive arteriovenous pressure measurement device.

In the Modification Example 1 of the noninvasive arteriovenous pressure measurement device (100a), as shown in FIG. 3, a gas bag (70a) as a stretchable bag-like object is arranged in the balloon (31a) of the pressing part (10a). By inflating or deflating the gas bag (70a), the pressure of the liquid (36a) supplied, in an amount regulated via the liquid volume regulating valve (18a), into the balloon (31a) is regulated. The pressurization of the liquid (36a) by the gas bag (70a) is effective in the cases where sufficient pressurization of the liquid (36a) cannot be achieved by the pressing button (32a) only. In the Modification Example 1, both the pressing button (32a) and the gas bag (70a) are provided. However, the measurement device may have not the pressing button (32a) but the gas bag (70a) only.

The pressure sensor (33a) is attached to a tube (71a) as a fluid passage (71) connected to the gas bag (70a). The tube (71a) is for allowing air (72) as the fluid that inflates or deflates the gas bag (70a) to flow into or out of the gas bag (70a).

The pressure sensor (33a) is arranged between the gas bag (70a) and a pressure regulating valve (73a) described later. In the Modification Example 1 of the noninvasive arteriovenous pressure measurement device (100a), only the liquid (36a) is enclosed in the balloon (31a). No air exists in the balloon (31a). Therefore, the inflation or deflation of the gas bag (70a) directly results in the increase or decrease in the liquid pressure in the balloon (31a). In the Modification Example 1 of the noninvasive arteriovenous pressure measurement device (100a), detecting the liquid pressure in the balloon (31a) can be achieved by detecting the air pressure in the gas bag (70a) using the pressure sensor (33a).

Here, in the Modification Example 1 of the noninvasive arteriovenous pressure measurement device (100a), air (72) is used as the fluid that flows into or out of the gas bag (70a). However, the fluid is not limited thereto and may be a liquid, for example.

The tube (71a) has a pressure regulating valve (73a) as a back-pressure regulating part (73). The pressure regulating valve (73a) is arranged such that the gas bag (70a) is located at the back-pressure side.

When the pressure regulating valve (73a) is opened, high-pressure air (72) flows into the gas bag (70a) from the air source (not shown), and the gas bag (70a) is inflated. After the pressure regulating valve (73a) is closed, the gas bag (70a) is kept in the inflated state. To increase the pressing force applied to the skin (61), the pressure regulating valve (73a) is opened to inflate the gas bag (70a) and thereby inflate the balloon (31a). The inflation of the balloon (31a) results in the increase in the pressing force onto the skin (61).

The tube (71a) has an outlet port (74a) for allowing air (72) to flow out of the gas bag (70a). The outlet port (74a) is located between the gas bag (70a) and the pressure regulating valve (73a). An open-close valve (75a) is attached to the outlet port (74a) via the piping. One end of the open-close valve (75) is communicated with the outlet port (74a), and the other end is opened.

When the open-close valve (75a) is opened, air flows out of the gas bag (70a), and the gas bag (70a) is deflated. After the open-close valve (75a) is closed, air does not flow out of the gas bag (70a) any more, and the pressure at the time of closing the open-close valve (75a) is kept in the gas bag (70a). To decrease the pressing force applied to the skin (61), the open-close valve (75a) is opened to deflate the gas bag (70a) and thereby deflate the balloon (31a). The deflation of the balloon (31a) results in the decrease in the pressing force onto the skin (61).

As described above, the pressure in the balloon (31a) is measured using the pressure sensor (33a). At this time, due to the hydrostatic pressure of the liquid (36a) in the balloon (31a), when the position of the end of the tube (71) to which the pressure sensor (33a) is connected is close to the ground, the measured value tends to be high, and when the position is high, the measured value tends to be low. Therefore, the height of the pressure sensor (33a) should be the same as the height of the pressed vein or as close to the height of the vein as possible.

Furthermore, for fine adjustment, calibration is preferably carried out before the measurement of the arteriovenous pressure. In this calibration, the measured value of the pressure sensor (33a) at the time when the balloon (31a) contacts the skin is set to zero. Thereby, the arteriovenous pressure can be accurately measured with this pressure sensor (33a).

Modification Example 2 of the First Embodiment

The Modification Example 2 of the noninvasive arteriovenous pressure measurement device (100b) is different from the first embodiment in the means to pressurize the balloon (31b) in the pressing part (10b). Hereinafter, description will be made focusing on the difference. Since the Modification Example 2 also has a means to pressurize the balloon (31b) as with the Modification Example 1, arterial pressure in addition to venous pressure can be measured.

The Modification Example 2 of the noninvasive arteriovenous pressure measurement device (100b) is configured such that when the probe (20b) is pressed against the balloon (31b), the balloon (31b) bulges to the skin side. The balloon (31b) is pressed by the head part (23b) of the probe (20).

Figure 4:
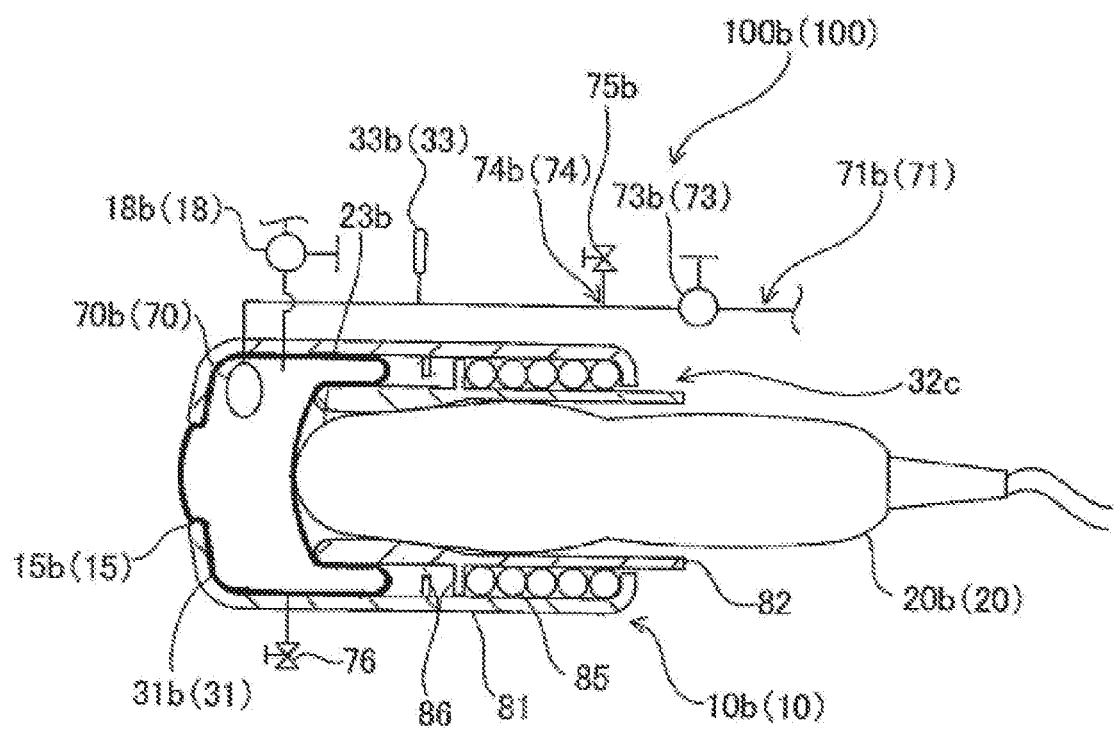
FIG. 4 shows the main part of Modification Example 2 of the first embodiment of the noninvasive arteriovenous pressure measurement device.

In the Modification Example 2 of the noninvasive arteriovenous pressure measurement device (100b), as shown in FIG. 4, an outer member is in the form of a bottomed cylinder (81) and an inner member is in the form of a cylinder (82) inserted in the outer member (81). The outer member (81) has an echo window (15b) in the bottom thereof, and the bottom part of the outer member (81) (the left side in FIG. 4) accommodates the balloon (31b). In the inner member (82), the probe (20b) is inserted.

The balloon (31b) accommodates a stretchable gas bag (70b) therein. A tube (71b) is connected to the gas bag (70b), and a pressure regulating valve (73b) and a pressure sensor (33b) are attached to the tube (71b). The tube (71b) has a gas outlet port (74b), and an open-close valve (75b) is attached to the piping connected to the outlet port (74b). Since the configuration for operating the pressure regulating valve (73b) and the open-close valve (75b) to inflate or deflate the gas bag (70b) is the same as that of the above Modification Example 1, the description will be omitted.

The liquid volume regulating valve (18b) for the balloon (31b) and the pressure regulating valve (73) for the gas bag (70b) are both provided outside the outer member (81). The liquid volume regulating valve (18b) and the pressure regulating valve (73) may be fixed on the outer surface of the outer member (81).

On the inner wall of the outer member (81), a ball spline (85) as an advancing and retreating mechanism for advancing and/or retreating the probe (20) relative to the balloon (31b) is attached. The ball spline (85) is provided for allowing the inner member (82) to move forward and backward relative to the outer member (81). In addition, a stopper (86) for preventing the inner member (82) from falling out of the outer member (81) is formed on the inner wall of the outer member (81) and the outer wall of the inner member (82).

In the Modification Example 2 of the noninvasive arteriovenous pressure measurement device (100b), by pushing the inner member (82) into the outer member (81), the probe (20b) held in the inner member (82) is pressed against the balloon (31b) in the outer member (81). As a result, the balloon (31b) transforms, and a part of the balloon (31b) bulges outward from the echo window (15b). The part of the balloon (31b) bulging outward from the echo window (15b) can be used to press the skin.

Figure 5A:
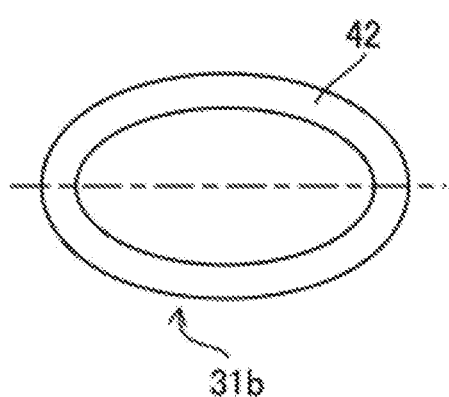
FIG. 5A is a front view and FIG. 5B is a side view.
Figure 5B:
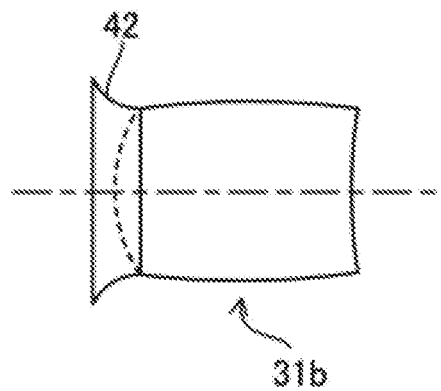

The balloon (31b) of the Modification Example 2 of the noninvasive arteriovenous pressure measurement device (100b) is, as shown in FIG. 5, in the shape of a tube with its both ends closed. The two ends of the balloon (31b) are elliptical. A flanged portion (42) is formed at one end of the balloon (31b). Tight contact of the flanged portion (42) with the inner surface of the outer member (81) securely fastens the balloon (31b) and the outer member (81).

The Modification Example 2 of the noninvasive arteriovenous pressure measurement device (100b) is more compact as compared to the first embodiment of the noninvasive arteriovenous pressure measurement device (100) because the Modification Example 2 does not have any pressing button (32). In addition, since the balloon (31b) is close to the measurement site, even when pressure calibration of the gas bag (70b) is forgotten after the tilt of the probe (20) relative to the ground surface is changed, measurement error hardly occurs.

Effects of the Embodiments

With use of the first embodiment of the noninvasive arteriovenous pressure measurement device (100), arterial pressure and venous pressure can be measured in a noninvasive and simple and convenient manner in a short period of time. The noninvasive arteriovenous pressure measurement device (100), unlike the measurement device of Non Patent Literature 1, can accurately measure arterial pressure and venous pressure at a site close to the body surface due to a solid and tight contact of the balloon (31) with the skin (61). The tight contact is achieved by placing the echo window (15) formed in an elliptical shape on the skin such that the major axis of the echo window (15) coincides with the longitudinal direction of the measurement site of the body.

The Modification Example 1 of the noninvasive arteriovenous pressure measurement device (100a) is provided with a gas bag (70a) as a mechanism for increasing the inner pressure of the balloon (31a), and therefore, can further increase the pressing force applied by the balloon (31a) to the skin (61). The increased pressing force applied by the balloon (31a) to the skin (61) enables the measurement of arterial pressure in addition to venous pressure.

With use of the Modification Example 1 of the noninvasive arteriovenous pressure measurement device (100a), the blood pressure in a superficial vein is measured under observation using the probe (20a), and unlike in the cases using a conventional ultrasound diagnostic device, the observation is made through the balloon (31a) containing a liquid permeable to ultrasound, the balloon (31a) being interposed between the superficial vein and the probe (20a).

The outside of the balloon (31a) is basically made of a flexible membrane, and the contact surface between the balloon (31a) and the superficial vein and the contact surface between the balloon (31a) and the probe (20a) (this does not apply to the cases where the balloon (31a) is integrated in the probe (20a)) have a membrane structure.

The ultrasound coming out of the probe (20a) passes through the membrane of the balloon (31a), water as a liquid permeable to ultrasound, and the membrane again, and enters the skin (61). The ultrasound is then reflected from the superficial vein or subcutaneous tissue, passes through the membrane and water as a liquid permeable to ultrasound, and returns, through the membrane, to the probe (20a), and then is subjected to image processing.

The structural feature of the first embodiment of the noninvasive arteriovenous pressure measurement device (100) lies in the balloon (31). When the pressure in the balloon (31) is increased, the pressure is applied, via the membrane of the flexible balloon (31), to a vein. As the vein is pressed by the pressure, the blood in the vein moves away to different sites in the blood vessel, and thus the lumen of the vein at the pressed site collapses.

As described above, the collapse of the vein occurs at the time when the pressure in the balloon (31) becomes equal to or slightly higher than the blood pressure in the vein. At this time, the pressure in the balloon (31) is detected with the pressure sensor (33) in the balloon (31). In the case of Modification Example 1, the pressure is detected with the pressure sensor (33a) connected to the tube (71a) of the gas bag (70a).

As the pressure in the balloon (31) increases, vein collapse occurs. Since the moment of the collapse can be observed with the probe (20), the pressure in the balloon (31) at the moment of the vein collapse can be measured with the pressure sensor (33), that is, the venous pressure in the superficial vein can be measured. When the echo image at the moment of the vein collapse is subjected to image processing including image recognition and identification by a computer and coupled with the measured value by the pressure sensor, more accurate measurement of venous pressure can be achieved.

Thus, according to the first embodiment of the noninvasive arteriovenous pressure measurement device (100), due to the combination of the balloon (31), the pressing button (32), the pressure sensor (33), and the probe (20), the pressure of the intended superficial vein can be measured in a simple and convenient manner in a short period of time.

To measure the central venous pressure, supine position may be employed. In the supine position, a part of the external jugular vein is generally almost at the same height as the anterior axillary line as the standard in the measurement of the central venous pressure, and therefore, by pressing the external jugular vein at the height that is as close as possible to the height of the anterior axillary line and carrying out observation, the central venous pressure can be easily measured. Also, the superficial vein pressure in the leg can also be easily measured as many times as desired in different body positions, such as standing position and supine position.

In the first embodiment of the noninvasive arteriovenous pressure measurement device (100), the pressing part (10) is attached to the probe (20) to enable the noninvasive venous pressure measurement. It is also possible that a structure having a similar constituent to the pressing part (10) is integrated in the probe (20).

As described above, the balloon (31) is accommodated in the casing (11) of the pressing part (10), and the contact surfaces of the balloon (31) with the patient and with the probe (20) are made of the flexible membrane.

By gradually pressing the pressing button (32) to gradually press the balloon (31), the inner pressure of the balloon (31) is gradually increased. While the inner pressure of the balloon (31) is increased, a collapsing vein is observed using the probe (20). The pressure at the moment of the vein collapse is detected with the pressure sensor (33) and the detected value is shown on the display (50).

Other Embodiments

In the first embodiment of the noninvasive arteriovenous pressure measurement device (100), in addition to the method of pressurizing the pressure measurement part by pressing the balloon (31), pressurized water may be supplied into the balloon (31) through a tube (17) connected to the balloon (31).

In the first embodiment of the noninvasive arteriovenous pressure measurement device (100), the pressure sensor (33) is directly disposed in the liquid (36) contained in the balloon (31) to detect the pressure of the liquid (36), but the location of the pressure sensor is not limited thereto. The pressure sensor (33) may be disposed in a separated room formed in the balloon (31) or in another balloon disposed in the balloon (31).

In the first embodiment of the noninvasive arteriovenous pressure measurement device (100), the balloon (31) as a flexible container is entirely formed of a flexible material permeable to ultrasound, but the balloon is not limited thereto. It is also possible that only the contact surfaces of the balloon (31) with the patient and with the probe (20) are made of a flexible membrane made of a flexible material and the rest of the balloon (31) is covered with a hard wall.

The hard wall provided to the balloon (31) is configured so as to withstand the changes in the pressure of the flexible membrane made of a flexible material. In this case, the pressing button (32) is provided on the hard wall, and by gradually pressing the button, the inner pressure of the balloon (31) is increased, and a collapsing vein is observed using the probe (20). The pressure at the moment of the vein collapse is measured with the pressure sensor (33) attached in the balloon (31) and the measured value is shown on the display (50).

Pressing only a part of the wall of the balloon (31) may be insufficient for obtaining an appropriate pressure increase required for the measurement of venous pressure. In this case, the inner pressure of the balloon (31) is regulated by supplying a compressible fluid to the balloon (31) along with appropriately discharging the supplied fluid, i.e., balancing the supplied amount and the discharged amount of the compressible fluid.

When the compressible fluid supplied to the balloon (31) for increasing the pressure of the balloon (31) is a gas, another balloon or a syringe may be disposed in the balloon (31) to prevent the gas from entering the liquid in the balloon (31). By injecting the gas into the balloon or the syringe, the pressure of the balloon (31) can be increased without bringing the gas into contact with the liquid in the balloon (31).

In the cases where the pressure sensor (33) is capable of directly detecting the pressure of the liquid (36) in the balloon (31), the pressure sensor (33) may be disposed in the balloon (31). In the cases where the pressure sensor (33) is not capable of directly detecting the pressure of the liquid (36) in the balloon (31), another balloon or a separated room is provided at a position in the balloon (31) not in the path of the ultrasound. The material and the structure of the balloon or the separated room should be selected such that the pressure in the balloon or the separated room can be held at almost the same level as the pressure of the liquid (36) in the balloon (31). Also, the pressure sensor (33) may be connected to a tube extending from the inside of the balloon or the separated room to the outside of the casing (11) of the pressing part (10).

The volume of the gas in the balloon or the separated room must be determined such that the pressure in the balloon or the separated room at the time of calibration can be zero. Also, to prevent the balloon or the separated room from bursting, the volume of the gas in the balloon or the separated room must be not more than the volume at the time when the balloon or the separated room inflates to the maximum extent without any pressure increase.

To achieve this, a volume adjusting mechanism, such as a syringe, should be provided at a site directly or indirectly connected to the balloon provided in the balloon (31) or to the separated room in the balloon (31). When the pressure is measured, pressure calibration is required. At this time, due to the hydrostatic pressure of the liquid (36) filling the balloon (31), when the position of the pressure sensor (33) or the position of one end of the tube connected to the pressure sensor located outside or inside the balloon (31) is close to the ground, the measured value tends to be high, and when the position is high, the measured value tends to be low.

Therefore, the height of the pressure sensor (33) should be basically the same as the height of the pressed vein or as close to the height of the vein as possible. Furthermore, for fine adjustment, calibration should be carried out before the measurement. To facilitate this, a calibration switch to start the calibration is provided.

With use of the first embodiment of the noninvasive arteriovenous pressure measurement device (100), noninvasive venous pressure measurement at various sites can be achieved in a few seconds, and repeated measurement can also be easily performed. Furthermore, in this echography, unlike in the cases where veins are observed using a hard probe for conventional echography, superficial veins are observed using a soft and flexible contact part in conditions where the pressure of the balloon (31) made of a flexible material is not increased. Therefore, the superficial veins are less likely to collapse, and the likelihood of overlooking in preoperative examination is reduced.

Regarding the noninvasive arterial pressure measurement, the principle is basically the same as that of general measurement based on air pressure. That is, in an artery pressed by a pressure not less than the systolic pressure, the blood does not flow. In an artery pressed by a pressure not less than the diastolic pressure and less than the systolic pressure, the blood flows only in a part of the systolic phase and does not flow in the diastolic phase. In an artery pressed by a pressure less than the diastolic pressure, the blood flows through the entire cycle of the systolic phase and the diastolic phase.

Using the principle, placing the balloon (31) at an artery close to the skin or a nutrient artery of the skin, arterial pressure is measured. The probe (20) with the pressing part (10) attached thereto is placed on the skin above the artery to be measured, and the pressure of the balloon (31) is increased by pressing the pressing button (32) in the pressing part (10) or by a pressure increasing mechanism for the balloon (31) provided inside or outside the pressing part (10) (for example, the gas bag (70*a*) in Modification Example 1) to press the artery at a site to be measured with the echo diagnostic device.

The pressure at the time when the arterial blood flow loses continuity with increase in the pressure of the balloon (31) is the diastolic pressure, and the pressure at the time when the blood flow completely stops is the systolic pressure. Thus, comparing the pressure of the balloon (31) at the pressing part (10) and the blood flow in the artery, the systolic pressure and the diastolic pressure are measured.

The moment when the arterial blood flow loses continuity (the measured value is equal to the diastolic pressure) and the moment when the blood flow completely stops (the measured value is equal to the systolic pressure) can be judged by simply observing a video showing artery pulsation based on echo images (B mode images). However, when the echo image is subjected to image processing including recognition and judgement by a computer and coupled with the measured value by the pressure sensor, more accurate measurement of arterial pressure in the systolic phase and the diastolic phase can be achieved. Furthermore, when a Doppler method, such as color Doppler, power Doppler, pulse wave Doppler, and continuous wave Doppler, is used for detecting the blood flow in an artery, and the data is subjected to image processing by a computer or blood flow analysis by a computer, the moment when the arterial blood flow loses continuity (the measured value is equal to the diastolic pressure) and the moment when the blood flow completely stops (the measured value is equal to the systolic pressure) can be recognized, and by coupling the recognition with the measured value by the pressure sensor, more accurate measurement of arterial pressure in the systolic phase and the diastolic phase can be achieved.

By using B-mode (brightness mode) in which a two-dimensional array of echo intensities as a result of ultrasound beam scanning is viewed as a static image or a moving image, the two-dimensional shape or movement of a measured site can be directly observed. However, in B-mode, periodicity of a movement cannot be read from the image. By a method in which multiple frames of B-mode image are computed in an image processor to extract the intensities of certain frequency components for obtaining pulsating frequency, the intensity of a periodic movement can be determined. Therefore, based on the pressure value detected at the detecting part (33) of the noninvasive arteriovenous pressure measurement device (100) and on the pulsating frequency, arterial pressures at the diastolic phase and the systolic phase can be measured. In this case, in addition to the method of pressurizing the pressure measurement part by pressing the balloon (31), a method in which pressurized water is supplied into the balloon (31) through a tube (17) connected to the balloon (31) may be employed.

The pressing part (10) is configured to comprise at least one of an advancing and retreating mechanism exemplified by the ball spline (85), the pressing button (32), and the stretchable bag-like object (70) with a fluid passage (71).

As shown in the first embodiment of the noninvasive arteriovenous pressure measurement device (100), the device may be configured such that the inner pressure of the balloon (31) is increased to press the skin, by pressing the balloon (31) at the pressing part (10). Alternatively, the device may be configured such that the inner pressure of the balloon (31) is increased to press the skin, by allowing pressurized fluid to flow into the balloon (31) via a tube connected to the balloon (31).

In the noninvasive arteriovenous pressure measurement device of the present invention comprising a probe for radiating ultrasound toward a blood vessel in the skin, a pressing part for pressing the skin, and a pressing force detecting part, the probe and the pressing part may be separated and exist as individual structures, or integrated into one structure. However, to reduce the cost of the device, as described in the above embodiment, the probe and the pressing part are preferably separated.

INDUSTRIAL APPLICABILITY

As described above, the present invention is useful for an arteriovenous pressure measurement device which allows noninvasive and accurate measurement of arteriovenous pressure.

REFERENCE SIGNS LIST

11 Casing
20 Probe
31 Balloon (Flexible container)
32 Pressing button
33 Pressure sensor (Detecting part)
36 Water (Liquid)
40 Processing part
50 Display
61 Skin
62 Blood vessel
100 Noninvasive arteriovenous pressure measurement device

The invention claimed is:

1. An arteriovenous pressure measurement method using a noninvasive arteriovenous pressure measurement device, the device comprising
a probe for radiating ultrasound toward a blood vessel in a skin,
a pressing part for pressing the skin in a state of being placed between the skin and the probe,
a detecting part for detecting a pressing force applied to the skin at the pressing part, and
an image processor,
the pressing part having a liquid permeable to the ultrasound and a flexible container accommodating the liquid, the flexible container being made of a flexible material permeable to the ultrasound,
the method comprising:
pressing the skin with a part of the outer surface of the flexible container, the part being in the path of the ultrasound,
radiating ultrasound toward a blood vessel in the skin for obtaining echo signals from reflected ultrasound,
scanning and processing the echo signals using the image processor for obtaining a B-mode image,
arithmetically processing a plurality of frames of the B-mode image using the image processor to extract the intensities of certain frequency components for obtaining a pulsating frequency, and
determining a diastolic pressure and a systolic pressure of the artery based on the pressure value detected by the detecting part and the pulsating frequency.

2. A noninvasive arteriovenous pressure measurement device comprising:
a probe for radiating ultrasound toward a blood vessel in a skin,
a pressing part for pressing the skin in a state of being placed between the skin and the probe, and
a detecting part for detecting a pressing force applied to the skin at the pressing part, the pressing part having a liquid permeable to the ultrasound and a flexible container accommodating the liquid, the flexible container being made of a flexible material permeable to the ultrasound, wherein a part of the outer surface of the flexible container, the part being in the path of the ultrasound, presses the skin,
wherein the detecting part detects the pressure of the liquid in the flexible container as the pressing force and the pressing part comprises an advancing and retreating mechanism for advancing or retreating the probe relative to the flexible container.

3. A noninvasive arteriovenous pressure measurement device comprising:
a probe for radiating ultrasound toward a blood vessel in a skin,
a pressing part for pressing the skin in a state of being placed between the skin and the probe, and
a detecting part for detecting a pressing force applied to the skin at the pressing part, the pressing part having a liquid permeable to the ultrasound and a flexible container accommodating the liquid, the flexible container being made of a flexible material permeable to the ultrasound, wherein a part of the outer surface of the flexible container, the part being in the path of the ultrasound, presses the skin, wherein the detecting part detects the pressure of the liquid in the flexible container as the pressing force and the pressing part comprises a pressing button for pressing the outer surface of the flexible container at a part not in contact with the skin.

4. A noninvasive arteriovenous pressure measurement device comprising:

a probe for radiating ultrasound toward a blood vessel in a skin, a pressing part for pressing the skin in a state of being placed between the skin and the probe, and a detecting part for detecting a pressing force applied to the skin at the pressing part, the pressing part having a liquid permeable to the ultrasound and a flexible container accommodating the liquid, the flexible container being made of a flexible material permeable to the ultrasound, wherein a part of the outer surface of the flexible container, the part being in the path of the ultrasound, presses the skin, wherein the detecting part detects the pressure of the liquid in the flexible container as the pressing force and the pressing part comprises a stretchable bag-like object in the flexible container accommodating the liquid and a fluid passage for allowing a fluid to flow into or out of the bag-like object.

5. A noninvasive arteriovenous pressure measurement device comprising:

a probe for radiating ultrasound toward a blood vessel in a skin, a pressing part for pressing the skin in a state of being placed between the skin and the probe, and a detecting part for detecting a pressing force applied to the skin at the pressing part, the pressing part having a liquid permeable to the ultrasound and a flexible container accommodating the liquid, the flexible container being made of a flexible material permeable to the ultrasound, wherein a part of the outer surface of the flexible container, the part being in the path of the ultrasound, presses the skin, wherein the detecting part detects the pressure of the liquid in the flexible container as the pressing force and the pressing part comprises a stretchable bag-like object in the flexible container accommodating the liquid and a fluid passage for allowing a fluid to flow into or out of the bag-like object and the fluid passage comprises a back-pressure regulating part for regulating the back pressure of the fluid, and the inner pressure of the bag-like object is regulated by the back-pressure regulating part.

6. A noninvasive arteriovenous pressure measurement device comprising:

a probe for radiating ultrasound toward a blood vessel in a skin, a pressing part for pressing the skin in a state of being placed between the skin and the probe, and a detecting part for detecting a pressing force applied to the skin at the pressing part, the pressing part having a liquid permeable to the ultrasound and a flexible container accommodating the liquid, the flexible container being made of a flexible material permeable to the ultrasound, wherein a part of the outer surface of the flexible container, the part being in the path of the ultrasound, presses the skin, wherein the detecting part detects the pressure of the liquid in the flexible container as the pressing force and the pressing part comprises a stretchable bag-like object in the flexible container accommodating the liquid and a fluid passage for allowing a fluid to flow into or out of the bag-like object and the fluid passage has an outlet port for allowing the fluid to flow out of the bag-like object.

7. A noninvasive arteriovenous pressure measurement device comprising:

a probe for radiating ultrasound toward a blood vessel in a skin, a pressing part for pressing the skin in a state of being placed between the skin and the probe, and a detecting part for detecting a pressing force applied to the skin at the pressing part, the pressing part having a liquid permeable to the ultrasound and a flexible container accommodating the liquid, the flexible container being made of a flexible material permeable to the ultrasound, wherein a part of the outer surface of the flexible container, the part being in the path of the ultrasound, presses the skin, wherein the detecting part detects the pressure of the liquid in the flexible container as the pressing force and a casing accommodating the flexible container is provided, the casing has a contact surface to be brought into contact with the skin, an ultrasound passing aperture is formed on the contact surface to allow the ultrasound that has passed through the flexible container and the liquid to pass the aperture, the outer surface of the flexible container presses the skin through the ultrasound passing aperture, and the outer periphery of the ultrasound passing aperture has an elliptical shape, a rectangular shape, or a rectangle-like shape having four rounded corners, and the flexible container has a tubular shape, and a flanged portion is formed at one axial end of the flexible container to allow close contact with the outer periphery of the ultrasound passing aperture on the inner surface of the casing.

* * * * *

UNITED STATES PATENT AND TRADEMARK OFFICE
CERTIFICATE OF CORRECTION

| | |
|---|---|
| PATENT NO. | : 11,000,258 B2 |
| APPLICATION NO. | : 15/757617 |
| DATED | : May 11, 2021 |
| INVENTOR(S) | : Hiroshi Tomoeda |

Page 1 of 1

It is certified that error appears in the above-identified patent and that said Letters Patent is hereby corrected as shown below:

On the Title Page

In Column 1, item (54), Title, Line 1, delete "NONINVESIVE" and insert -- NONINVASIVE --.

In the Specification

In Column 1, Line 1, delete "NONINVESIVE" and insert -- NONINVASIVE --.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*